United States Patent
Limonadi

(10) Patent No.: US 9,799,187 B2
(45) Date of Patent: Oct. 24, 2017

(54) METHOD AND APPARATUS FOR LIMITING RANGE OF MOTION OF BODY

(71) Applicant: Farhad M. Limonadi, Rancho Mirage, CA (US)

(72) Inventor: Farhad M. Limonadi, Rancho Mirage, CA (US)

(*) Notice: Subject to any disclaimer, the term of this patent is extended or adjusted under 35 U.S.C. 154(b) by 725 days.

(21) Appl. No.: 13/763,407

(22) Filed: Feb. 8, 2013

(65) Prior Publication Data

US 2013/0201021 A1     Aug. 8, 2013

Related U.S. Application Data

(60) Provisional application No. 61/596,687, filed on Feb. 8, 2012.

(51) Int. Cl.
   *G08B 23/00*     (2006.01)
   *G08B 21/02*     (2006.01)
   (Continued)

(52) U.S. Cl.
   CPC ............ *G08B 21/02* (2013.01); *A61B 5/1071* (2013.01); *A61B 5/1116* (2013.01);
   (Continued)

(58) Field of Classification Search
   CPC . G08B 21/02; A63B 21/4007; A63B 21/0004; A63B 21/0407; A63B 23/0244;
   (Continued)

(56) References Cited

U.S. PATENT DOCUMENTS

| | | |
|---|---|---|
| 4,938,476 A | 7/1990 | Brunelle et al. |
| 5,042,505 A | 8/1991 | Mayer et al. |

(Continued)

FOREIGN PATENT DOCUMENTS

| | | |
|---|---|---|
| KR | 10-2010-0089539 A | 8/2010 |
| KR | 20-2011-0002122 U | 3/2011 |

(Continued)

OTHER PUBLICATIONS

International Search Report and Written Opinion for corresponding PCT Application No. PCT/US2013/025415, dated May 15, 2013, issued by the International Searching Authority (8 pages).

(Continued)

*Primary Examiner* — Fekadeselassie Girma
*Assistant Examiner* — Royit Yu
(74) *Attorney, Agent, or Firm* — Klarquist Sparkman, LLP

(57) ABSTRACT

The present invention relates to apparatus and methods for warning a user about undesirable motion of a first portion of the user's body relative to a second portion of the user's body. In one representative embodiment, an apparatus for warning a user about motion of a first portion of the user's body relative to a second portion of the user's body comprises at least one sensor configured to measure the angle of the first portion of the user's body relative to a reference. The sensor is configured to be worn on the user's body, and is in communication with a controller. A warning mechanism is also in communication with the controller, and the controller is operable to activate the warning mechanism upon movement of the first portion of the user's body relative to the second portion of the user's body beyond a predetermined angle relative to the reference.

22 Claims, 9 Drawing Sheets

(51) Int. Cl.

| | | |
|---|---|---|
| *A61B 5/00* | (2006.01) | |
| *A61B 5/107* | (2006.01) | |
| *A61B 5/11* | (2006.01) | |
| *A63B 23/02* | (2006.01) | |
| *A63B 21/00* | (2006.01) | |
| *A63B 21/04* | (2006.01) | |
| *A63B 24/00* | (2006.01) | |
| *A63B 71/06* | (2006.01) | |

(52) U.S. Cl.
CPC .......... *A61B 5/6831* (2013.01); *A61B 5/7405* (2013.01); *A61B 5/746* (2013.01); *A63B 21/0004* (2013.01); *A63B 21/0407* (2013.01); *A63B 21/4007* (2015.10); *A63B 23/0244* (2013.01); *A63B 24/0087* (2013.01); *A63B 2071/0627* (2013.01); *A63B 2220/16* (2013.01); *A63B 2220/801* (2013.01); *A63B 2220/836* (2013.01); *A63B 2225/093* (2013.01); *A63B 2225/50* (2013.01)

(58) Field of Classification Search
CPC ........ A63B 24/0087; A63B 2071/0627; A63B 2220/16; A63B 2220/836; A63B 2225/093; A63B 2225/50; A61B 5/1071; A61B 5/1116; A61B 5/7405; A61B 5/746
USPC ....... 340/540, 573.7; 600/594; 128/781–782; 73/1.38
See application file for complete search history.

(56) References Cited

U.S. PATENT DOCUMENTS

| | | | | |
|---|---|---|---|---|
| 5,143,088 | A * | 9/1992 | Marras et al. | 600/594 |
| 5,221,088 | A * | 6/1993 | McTeigue et al. | 473/201 |
| 5,337,758 | A * | 8/1994 | Moore et al. | 600/594 |
| 5,398,697 | A * | 3/1995 | Spielman | 600/594 |
| 5,469,861 | A | 11/1995 | Piscopo et al. | |
| 5,513,651 | A | 5/1996 | Cusimano et al. | |
| 5,640,971 | A * | 6/1997 | Martin, Jr. | 600/594 |
| 5,772,610 | A * | 6/1998 | McGorry et al. | 600/594 |
| 6,146,312 | A * | 11/2000 | Sclichter | 482/4 |
| 6,234,982 | B1 * | 5/2001 | Aruin | 600/595 |
| RE37,209 | E | 6/2001 | Hensley et al. | |
| 6,334,852 | B1 | 1/2002 | Seyl | |
| 6,402,708 | B1 | 6/2002 | Sitte | |
| 6,517,501 | B1 | 2/2003 | Slautterback | |
| 6,592,538 | B1 | 7/2003 | Hotchkiss et al. | |
| 6,723,061 | B2 | 4/2004 | Williams | |
| 6,834,436 | B2 | 12/2004 | Townsend et al. | |
| 6,852,067 | B2 | 2/2005 | Limonadi | |
| 7,210,240 | B2 | 5/2007 | Townsend et al. | |
| 7,431,703 | B2 * | 10/2008 | Salvi et al. | 600/594 |
| 7,698,830 | B2 | 4/2010 | Townsend et al. | |
| 7,850,574 | B2 | 12/2010 | Narayanaswami | |
| 8,025,632 | B2 | 9/2011 | Einarsson | |
| 2001/0020140 | A1 | 9/2001 | Kramer | |
| 2001/0031937 | A1 | 10/2001 | Repice et al. | |
| 2004/0073987 | A1 * | 4/2004 | Jansen | 2/422 |
| 2005/0070830 | A1 * | 3/2005 | Schultz | 602/19 |
| 2005/0237209 | A1 * | 10/2005 | Van Dongen | 340/573.7 |
| 2006/0112754 | A1 * | 6/2006 | Yamamoto et al. | 73/1.38 |
| 2008/0091082 | A1 * | 4/2008 | Lu | 600/300 |
| 2008/0319364 | A1 * | 12/2008 | Josey | 602/19 |
| 2009/0135009 | A1 * | 5/2009 | Little et al. | 340/540 |
| 2010/0249667 | A1 | 9/2010 | Narayanaswami | |
| 2011/0046518 | A1 * | 2/2011 | Fischer | 600/594 |
| 2011/0063114 | A1 * | 3/2011 | Ikoyan | 340/573.7 |
| 2011/0073450 | A1 * | 3/2011 | Wass | 200/331 |
| 2011/0306471 | A1 | 12/2011 | Huang | |
| 2012/0179418 | A1 * | 7/2012 | Takasugi et al. | 702/151 |
| 2013/0072829 | A1 | 3/2013 | Fausti et al. | |

FOREIGN PATENT DOCUMENTS

| | | |
|---|---|---|
| KR | 10-2011-0135165 A | 12/2011 |
| WO | WO/00/076400 | 12/2000 |
| WO | WO-2001/037730 A1 | 5/2001 |
| WO | WO 01/49235 | 7/2001 |
| WO | WO/05/055815 | 6/2005 |

OTHER PUBLICATIONS

Office Action issued by the United States Patent and Trademark Office dated May 21, 2014, for related U.S. Appl. No. 13/557,113, 18 pp.

International Search Report and Written Opinion issued by the Korean Intellectual Property Office dated Sep. 5, 2013, for related PCT Patent Application No. PCT/US2013/045364, 10 pp.

* cited by examiner

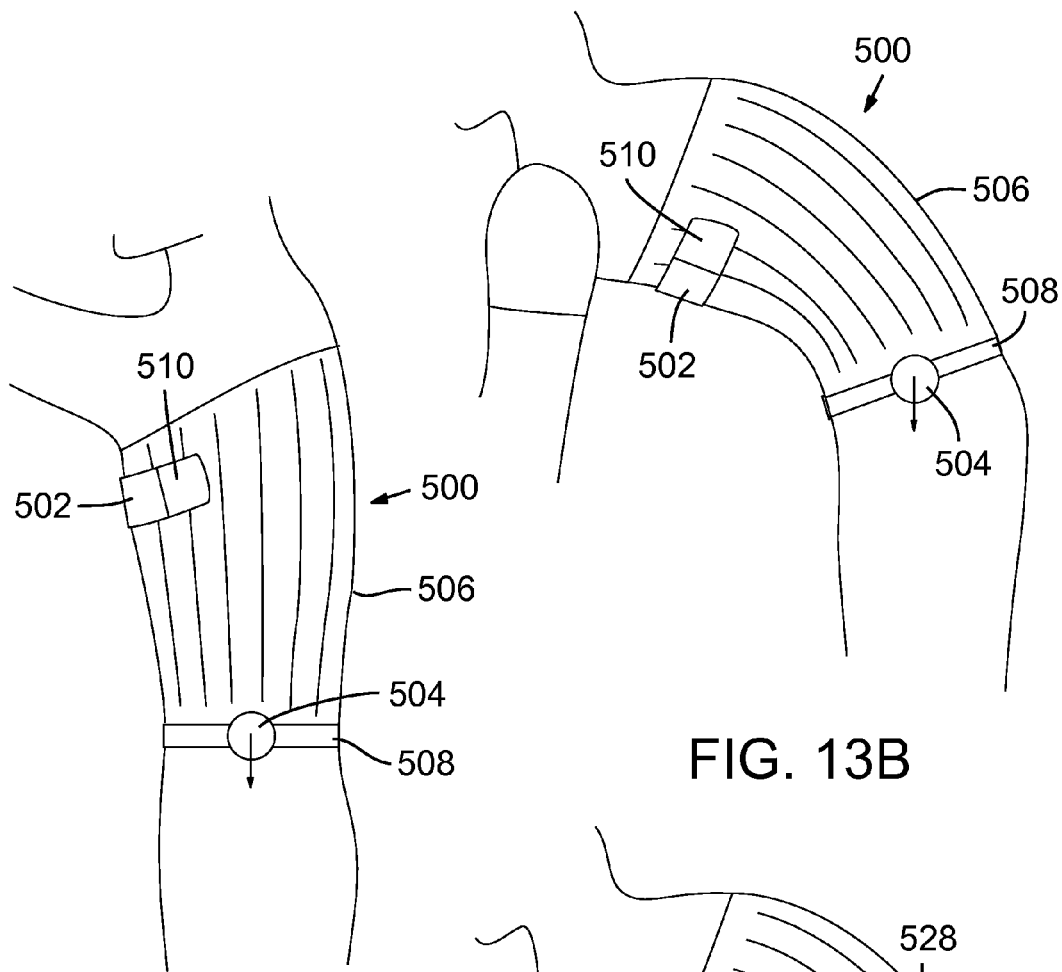
FIG. 13A
FIG. 13B
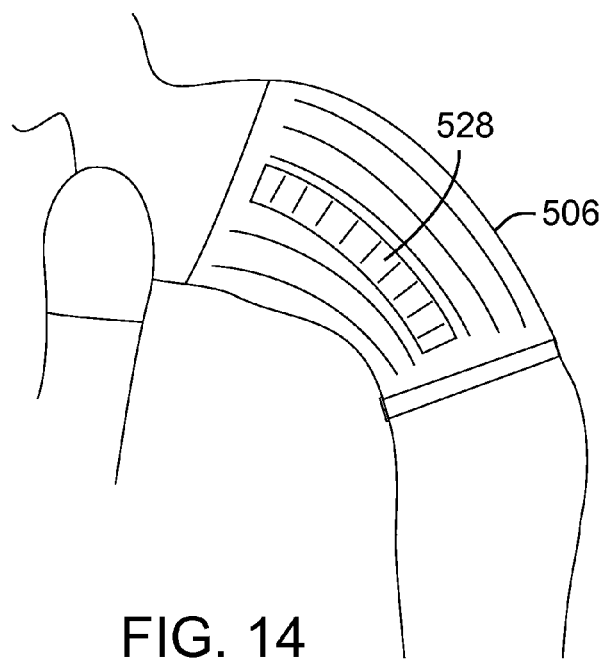
FIG. 14

_US 9,799,187 B2_

METHOD AND APPARATUS FOR LIMITING RANGE OF MOTION OF BODY

CROSS REFERENCE TO RELATED APPLICATION

The present application claims the benefit of U.S. Provisional Application No. 61/596,687, filed Feb. 8, 2012, which is incorporated herein by reference.

FIELD

The present invention relates to apparatus and methods for warning a user about undesirable motion of a first portion of the user's body relative to a second portion of the user's body.

BACKGROUND

Poor posture, such as the hunching forward of the neck, shoulders, or lower back, contributes to chronic back pain and can result in semi-permanent sagittal misalignment of the spine, or sagittal imbalance. Poor posture during normal activities such as sitting, standing, walking, or lifting of heavy objects, leads to straining of certain muscles of the back and disuse of others. Over time, this leads to weakening of the posterior tension band as certain muscles attempt to compensate for the misalignment of the spine, while others atrophy from disuse. As the posterior tension band weakens, maintaining correct posture becomes more difficult, causing a person to hunch forward. This condition is compounded by the gradual decline in strength of the muscles and bones of the back associated with aging. This loss of the ability to maintain correct posture can cause chronic back pain, and increase the risk of back injury during normal activities, such as lifting or carrying of objects. Furthermore, once the strength of the posterior tension band begins to deteriorate, the condition is difficult to correct.

Conventional techniques and devices for correcting sagittal imbalance often require that a user's range of motion be severely limited, or that their back be immobilized. In this manner, conventional devices force the user to maintain correct posture. However, these devices can unnecessarily limit a user's ability to perform activities during work or daily life that would not otherwise implicate or aggravate sagittal imbalance.

SUMMARY

Several embodiments of devices and methods are shown and described herein directed to warning a user about undesirable motion of a first portion of the user's body relative to a second portion of the user's body. The disclosed embodiments are especially useful for warning a user about undesirable motion of the user's spine, and therefore are useful in assisting the user in maintaining proper posture. In one representative embodiment, an apparatus for warning a user about motion of a first portion of the user's body relative to a second portion of the user's body comprises at least one sensor configured to measure the angle of the first portion of the user's body relative to a reference. The sensor is configured to be worn on the user's body, and is in communication with a controller. A warning mechanism is also in communication with the controller, and the controller is operable to activate the warning mechanism upon movement of the first portion of the user's body relative to the second portion of the user's body beyond a predetermined angle relative to the reference.

Another representative embodiment comprises a method of warning a user about motion of a first portion of the user's body relative to a second portion of the user's body. The method comprises placing at least one sensor configured to measure the angle of the first portion of the user's body relative to a reference plane on the first portion of the user's body. The sensor detects motion of the first portion of the user's body relative to the second portion of the user's body by detecting the angle of the first portion of the user's body relative to the second portion of the user's body. If the angle exceeds a predetermined threshold, the user is provided with an audible, visual, or tactile warning.

In a third representative embodiment, an apparatus for maintaining a neutral orientation of a user's spine comprises a first mounting portion configured to be placed on an upper portion of the user's torso, a second mounting portion configured to be placed on a lower portion of the user's torso, and at least one elongated member interconnecting the first portion and the second portion. A switch mechanism is connected to an end portion of the elongated member, and the elongated member is configured to activate the switch mechanism upon extension or flexion of the spine beyond a predetermined range of motion. A warning mechanism is electrically coupled to the switch mechanism, and the switch mechanism is operable to activate the warning mechanism upon extension or flexion of the spine beyond the predetermined range of motion.

The foregoing and other objects, features, and advantages of the invention will become more apparent from the following detailed description, which proceeds with reference to the accompanying figures.

BRIEF DESCRIPTION OF THE DRAWINGS

FIG. 13A is a side elevation view of another apparatus for warning a user about undesirable motion of a first portion of the user's body relative to a second portion of the user's body being worn by a user.

FIG. 13B is a side elevation view of the user of FIG. 13B bending forward wearing the apparatus of FIG. 13B.

FIG. 14 is a side elevation view of an alternative embodiment of the apparatus of FIG. 13B being worn by a user.

DETAILED DESCRIPTION

A device and method are disclosed for limiting the range of motion of a first part of a user's body with respect to a second part of the user's body. The device is configured to permit the user to move the first part of their body relative to the second part of their body within a preset range of motion, which can be adjusted according to the particular requirements of the user. As the first part of the user's body approaches an undesirable or unsafe position or orientation relative to the second part of the user's body, the device employs one or more of a variety of warning mechanisms to alert the user. If the first and second parts of the user's body continue to move in an undesirable or unsafe manner relative to one another, the device can be configured to mechanically limit further motion. In this manner, the device is useful for assisting a user in maintaining a suitable orientation of two parts of a user's body when engaging in certain activities or recovering from injury. For example, the device can be used to maintain proper posture, and to maintain a suitable orientation of the back, knee, hip, elbow, wrist, neck, ankle, fingers, or any other joint.

In this application, "posture" refers to the orientation of the spine. "Proper posture" refers to a neutral spinal orientation wherein the erect skeleton bears the weight of the head and upper body with minimal muscular effort. "Poor posture" refers to any non-neutral spinal orientation wherein additional muscular effort is required to bear the weight of the head and upper body.

In this application, "lumbar region" refers to the portion of the spine comprising lumbar vertebrae.

In this application, "thoracic region" refers to the portion of the spine comprising thoracic vertebrae.

In this application, "normally open" means that the contacts of a switch are not electrically connected in a default state. "Normally closed" means that the contacts of a switch are electrically connected in a default state.

Figure 1:
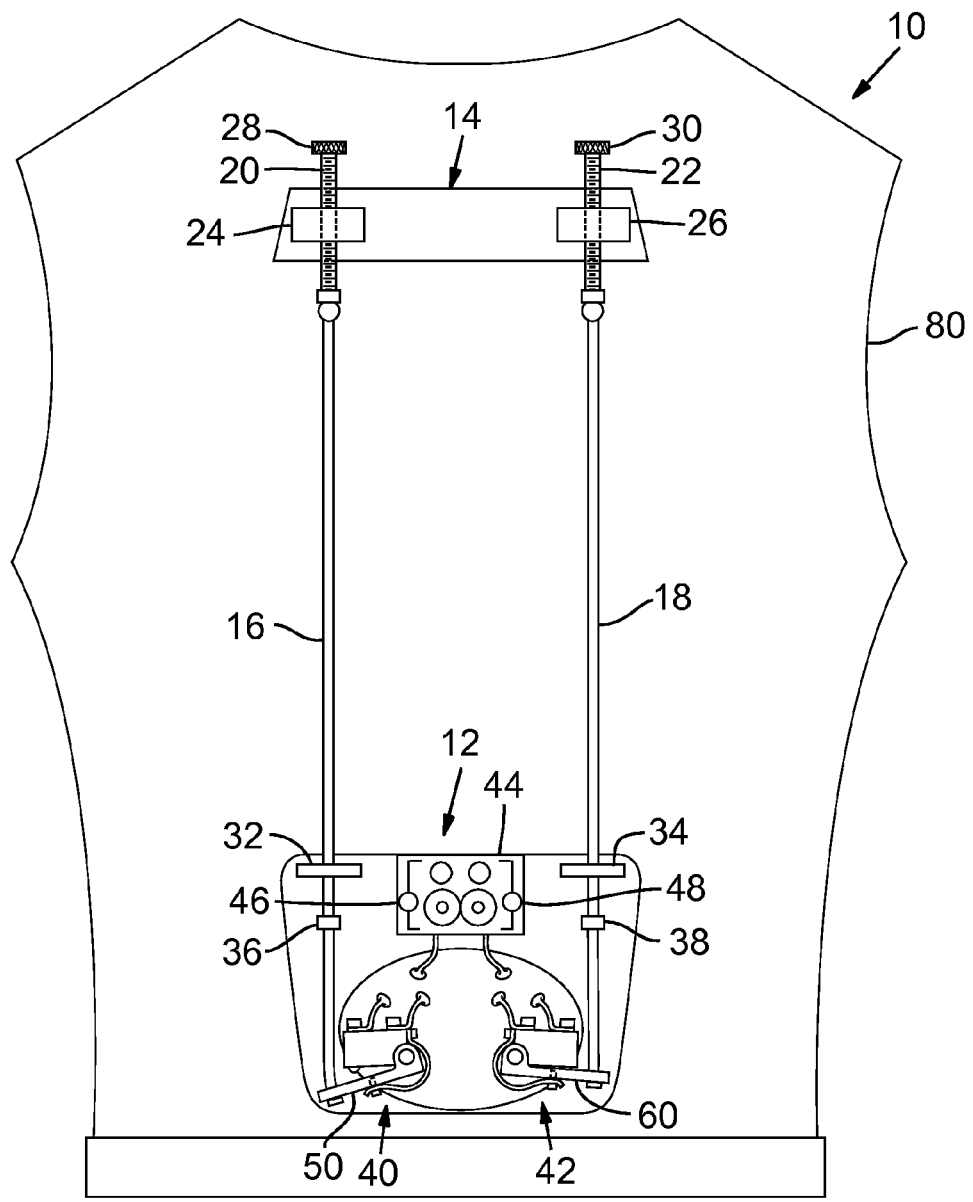
FIG. 1 is a plan view of an apparatus for warning a user about undesirable motion of a first portion of the user's body relative to a second portion of the user's body.

Referring to FIG. 1, there is shown a device 10 configured to be worn on a user's back to treat or prevent poor posture during activities such as sitting, standing, walking, or lifting of heavy objects. The device is configured to permit the user to move within a predetermined range of motion, and to alert the user as the user approaches an undesirable or unsafe posture. The range of motion can be adjusted according to the particular needs of the user. For example, the range of motion can be defined in accordance with the particular activity in which the user engages (e.g., lifting, bending forward, bending backward, sitting, etc.), the treatment of symptoms attendant to chronically poor posture (e.g., back pain, neck pain, stiffness, etc.), and/or a specific protocol to assist in recovering from injury or surgery. In particular embodiments, the device allows free range of motion of the back. In alternative embodiments, the device can mechanically limit the user from moving beyond the preset or predetermined range of motion. In this manner, the device allows a user to perform tasks that require modest amounts of flexion or extension, while warning the user about, and helping to prevent, harmful degrees of flexion or extension.

Figure 3:
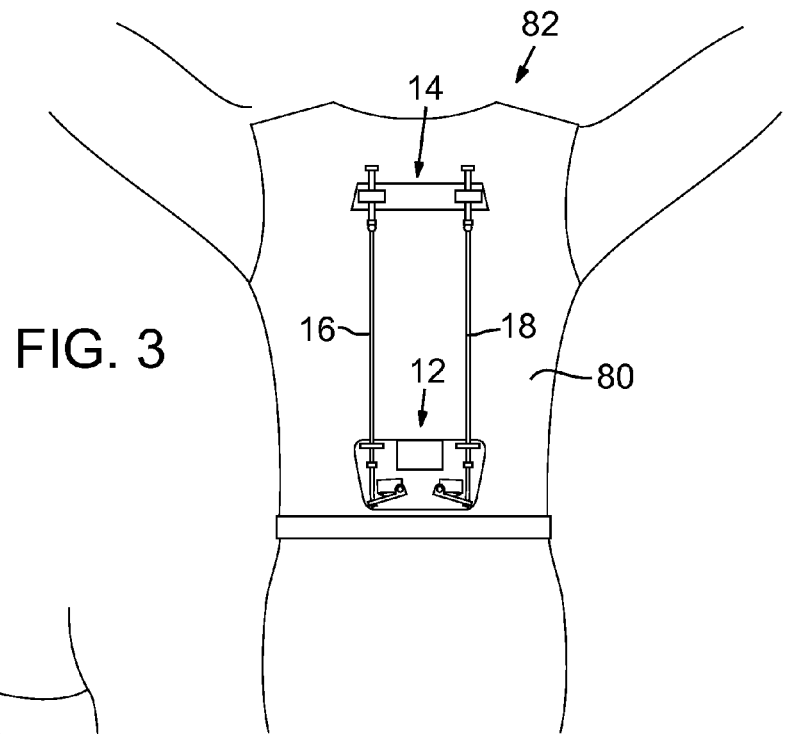
FIG. 3 is a side elevation view of the apparatus of FIG. 1 being worn on the back of a user.

The device 10 comprises a first mounting portion or mounting bracket 12 and a second mounting portion or mounting bracket 14 in a spaced-apart relationship. As shown in FIG. 3, the first mounting bracket 12 is configured to be placed on the lower back of a user generally over the lumbar region of the spine, and the second mounting bracket 14 is configured to be placed on the upper back of the user in the thoracic region generally between the shoulders. However, the first and second mounting brackets 12, 14 can be placed over any suitable region of the spine in order to regulate flexion and extension of that particular region. In this manner, the first and second mounting brackets 12, 14 move generally away from one another as the user flexes their back, and toward one another as the user extends their back. In the embodiment shown, the first and second mounting brackets 12, 14 are mounted on an upper body garment in the form of a vest 80 or other wearable device, which is worn by a user over or under the user's clothing. The vest 80 can be configured such that the vest moves substantially proportionally with the user's back as the user's back flexes and extends. In this manner, the first and second mounting brackets 12, 14 can travel substantially proportionally with the user's back as the vest 80 moves. In alternative embodiments, the device 10 can be attached directly to the user's clothing, or directly onto the user's body, such as with an adhesive.

The first and second mounting brackets 12, 14 are connected by elongated members in the form of cords 16, 18. Desirably, cords 16, 18 are elastic, and contract or elongate longitudinally as the first and second mounting brackets 12, 14 move toward or away from one another, respectively. The cords may be formed of any suitable elastic material, such as rubber or any of various elastomers. In the embodiment shown, the cords 16, 18 are anchored to the first mounting bracket 12. The device 10 is configured such that the cord 16 is in a substantially relaxed or slackened state in the case of proper posture, while the cord 18 is in a substantially tensioned state. In flexion (i.e., as the user bends forward), the cord 16 is subjected to tension corresponding to the degree of flexion as the first and second mounting brackets 12, 14 are drawn away from one another, while the cord 18 experiences correspondingly greater tension than in a state of proper posture. In extension (i.e., as the user bends backward), the cord 16 is in a relaxed or slackened state as the first and second mounting brackets 12, 14 are drawn toward one another, while the tension in the cord 18 is relieved corresponding to the degree of extension.

The length and tension of the cords 16, 18 can be adjusted by rods 20, 22, respectively, located on the second mounting bracket 14. In the embodiment shown, the rods 20, 22 are threaded, and are rotatably disposed in respective threaded openings in brackets 24, 26. The upper ends of the cords 16, 18 are connected to the lower ends of the rods 20, 22, respectively. The brackets 24, 26 are rigidly mounted to the second mounting bracket 14, such that rotating the rods 20, 22 causes them to travel in and out of the brackets 24, 26. The rods can further comprise knurled heads 28, 30 to facilitate rotation of the rods by a user. In this manner, the length and tension of the cords 16, 18 can be adjusted to achieve the desired range of motion.

The first mounting bracket 12 comprises a pair of range of motion limiters in the form of eyelets 32, 34, which are rigidly mounted on or formed in the first mounting bracket 12. A pair of adjustable stops in the form of annular disks 36, 38 are slidably disposed around the cords 16, 18, which extend freely though respective openings in the eyelets 32, 34. The annular disks 36, 38 are configured such that once positioned at the desired location along the length of the cords 16, 18, the annular disks 36, 38 are frictionally retained in their respective positions. In this manner, as the back flexes, the disks 36, 38 are pulled into engagement with the eyelets 32, 34, thereby resisting further elongation or movement of the cords and making it more difficult to continue further flexion of the back. In alternative embodiments, cords of varying degrees of elasticity can be used to achieve a desired range of motion. For example, highly elastic cords that provide little or no resistance to longitudinal elongation can be employed where the device is not intended to limit the range of motion of the back. Conversely, highly non-elastic cords that provide significant resistance to longitudinal elongation can be employed to mechanically limit the range of motion.

The first mounting bracket 12 further comprises a normally open switch 40 and a normally closed switch 42 in electrical communication with a controller 44. As used herein, "controller" refers to hardware logic components such as, for example, field-programmable gate arrays, programmable logic controllers, microcontrollers, microprocessors, or discrete electronic components configured to perform control functionality. The switches 40, 42 are configured to activate a warning mechanism to generate a warning signal, such as an audible signal, visual signal, tactile signal, or any combination thereof, to warn the user when the user is approaching an undesirable degree of flexion or extension. In the embodiment of FIG. 1, the switches 40, 42 activate warning mechanisms such as speakers 46, 48, respectively, mounted on and in communication with the controller 44. The two switches are similar to one another, except that the switch 40 is normally open due to the relaxed condition of the cord 16 while the switch 42 is normally closed due to the tensioned condition of the cord 18 when the user is in a state of proper posture.

Figure 2:
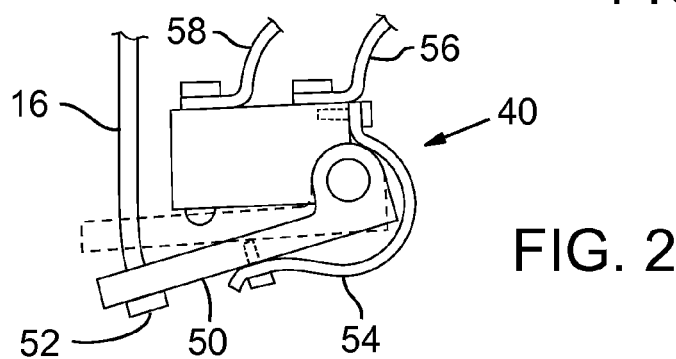
FIG. 2 is a magnified view of one of the switches of the apparatus of FIG. 1.

Only the switch 40 will now be described, with reference to FIG. 2. The switch 40 includes a pivotally moveable contact arm 50 which is attached at its distal end to the cord 16 by an enlarged end or fastener 52. A leaf spring 54 biases the contact arm 50 such that the contacts of the switch are normally open. When the user's back moves into a flexed position, the cord 16 pulls the contact arm 50 into its closed position for switching electrical power from a first lead 56 to a second lead 58, thereby causing the speaker 46 to generate an audible warning signal. With reference to FIG. 1, in a manner similar to switch 40, the spring-biased contact arm 60 of the switch 42 pulls the contacts of the switch 42 into the open position as the user's back extends and the tension in the cord 18 is relieved, thereby causing the speaker 48 to generate an audible warning signal. The switches 40, 42 can take the form of, for example, limit switches, micro switches, magnet switches, optical switches, etc. Also, the switches can be multi-position switches that can detect multiple positions of the back and activate the warning mechanisms to generate different warning signals as the user's back moves through different positions.

The speakers 46, 48 can be configured to provide a variety of audible warnings to the user. For example, as the degree of flexion or extension increases, the audible warning signal generated by the speakers can increase in volume. Alternatively, the speakers can generate various types of audible warning signals corresponding to increasing flexion or extension. The audible warning signals can also be combined with tactile signals, such as vibration or buzzing generated by a vibrator motor, or visual signals generated by, for example, light-emitting diodes (LEDs) or incandescent lights. Additionally, the switches 40, 42 can be configured to activate a single speaker rather than a pair of speakers, or a single vibrator motor rather than a pair of vibrator motors, etc. In alternative embodiments, one cord and switch mechanism can be disposed on the front of a user's torso and one cord and switch mechanism can be disposed on the back of a user's torso so as to limit and detect extension of the back as well as flexion.

Figure 11:
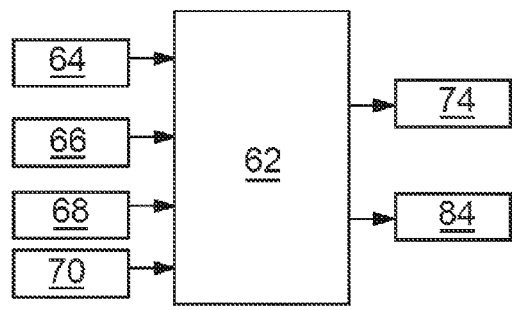
FIG. 11 is a schematic representation of a process performed by a controller.
Figure 12:
FIG. 12 is a schematic representation of an electromagnetic transmitter in communication with a receiver.

The controller 44 comprises circuit elements configured to execute the functionality shown in FIG. 11. A subroutine 62 includes at least one switch input 64, an alarm mode selector input 66, an ON/OFF switch input 68, and a time duration input 70. The switch input 64 provides signal input from the switches 40, 42. The alarm mode selector input 66 provides input from an alarm mode selector switch (not shown), allowing the user to set the type of warning signal generated. The ON/OFF switch input 68 turns the subroutine 62 from an OFF state to an ON state and vice versa. The time duration input 70 provides a user-inputted time duration for which a switch must be closed in order to trigger an alarm signal. The subroutine 62 further includes a warning signal output 74, which activates the speakers 46, 48, and a data output 84 wherein data such as time, date, and type of alarm signals (e.g., flexion, extension, etc.) can be outputted to non-transitory, computer-readable storage media or a computer for analysis. Additionally, the controller 44 can comprise a transmitter 76, which can generate a wireless signal, such as a radio, infrared, or bluetooth signal, to activate a remote warning device 78, as shown in FIG. 12. In alternative embodiments, the warning signal output 74 can activate various warning mechanisms (e.g., audible, visual, tactile, etc.).

Figure 4:
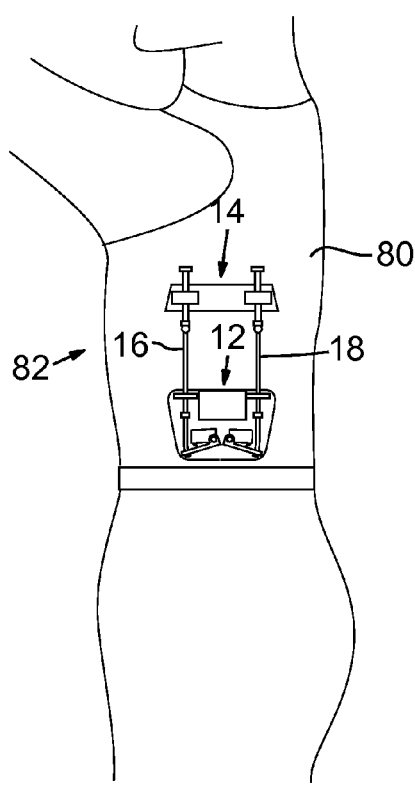
FIG. 4 is a side elevation view of the apparatus of FIG. 1 being worn on a side of the torso of a user.
Figure 5:
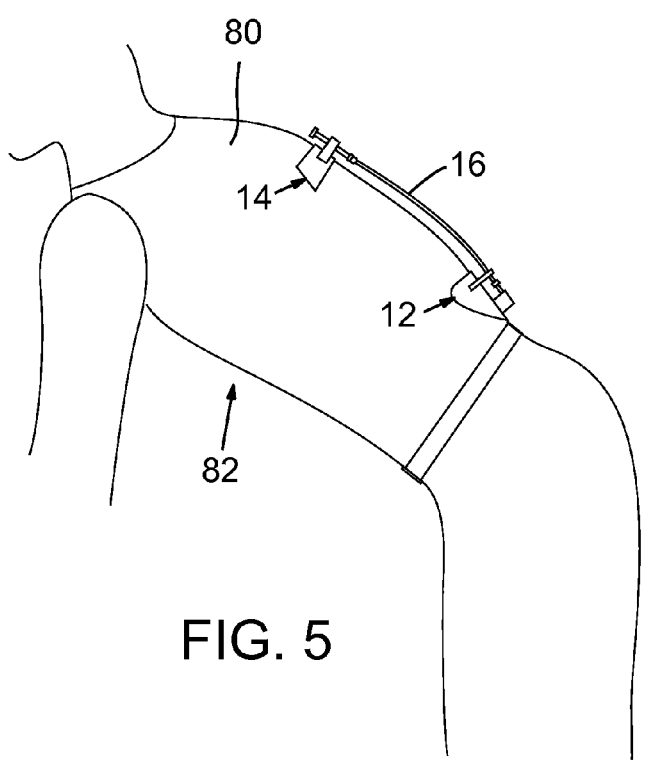
FIG. 5 is a side elevation view of the user of FIG. 3 bending forward while wearing the apparatus of FIG. 1.

Referring now to FIGS. 3, 4, and 5, the device 10 is shown mounted to the vest 80 being worn by a user 82. In FIGS. 3 and 5, the device 10 is shown being worn on the back of the user 82, where the device 10 can monitor flexion (FIG. 5) and extension. In a similar fashion, the device 10 can be configured to be worn on the side of a user's torso to monitor lateral flexion, as shown in FIG. 4 (i.e., bending side-to-side). In alternative embodiments, the device 10 can also be worn on the chest or abdomen of a user. In other embodiments, the device 10 can include only the cord 16 and the switch 40 for monitoring flexion. Similarly, the device 10 can include only the cord 18 and the switch 42 for monitoring extension.

Figure 6:
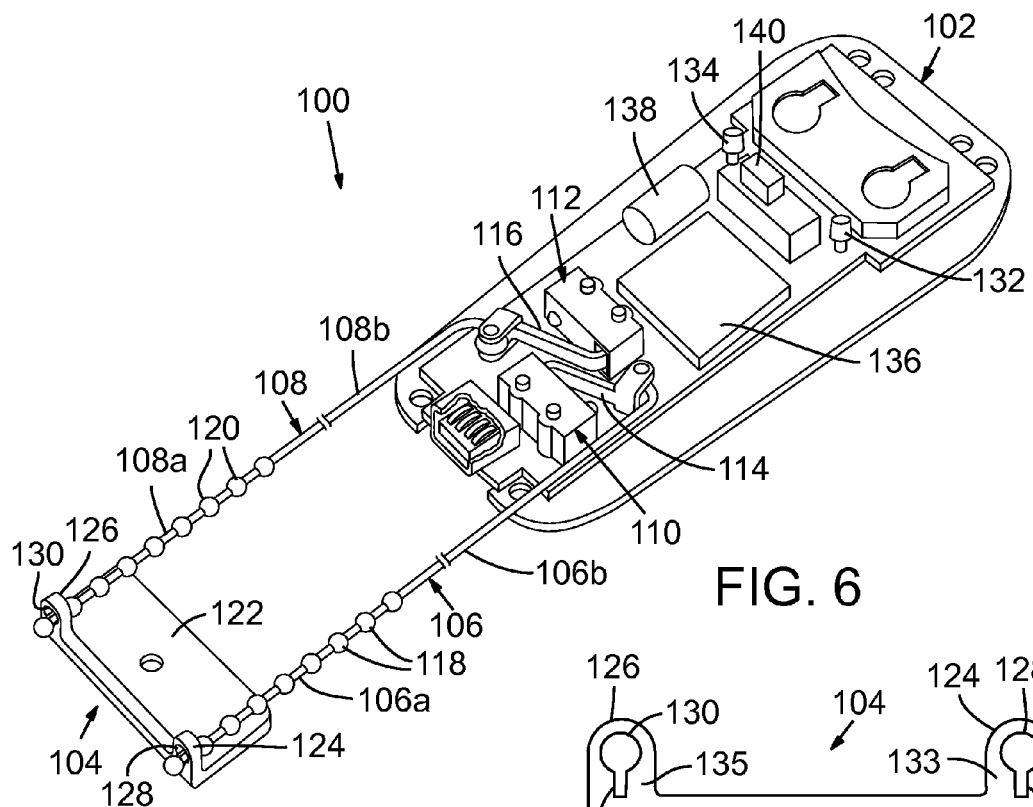
FIG. 6 is a pictorial view of another embodiment of an apparatus for warning a user about undesirable motion of a first portion of the user's body relative to a second portion of the user's body.

Referring to FIG. 6, there is shown a second embodiment of a device 100 configured to be worn on a user's back to treat or prevent poor posture. The device 100 is configured to be placed on the back of a user in a manner similar to the embodiment of FIG. 1 above. The device 100 comprises a first mounting portion or mounting bracket 102 and a second mounting portion or mounting bracket 104 arrayed in a spaced-apart relationship. Extension of the user's back causes the first and second mounting brackets 102, 104 to be drawn generally toward one another, and flexion of the user's back causes the first and second mounting brackets to be drawn generally away from one another. As with the embodiment of FIG. 1, the device 100 is configured to be mounted on a vest similar to the vest 80 of a flexible back brace or another type of wearable device, which can be worn by a user over or under the user's clothing. The device 100 can be mounted to the back, the front, or either side of the vest, as described above with respect to the embodiment of FIGS. 1-5. In alternative embodiments, the device 100 can be attached directly to the user's clothing, or directly to the user's body.

The first and second mounting brackets 102, 104 are interconnected by parallel elongated members in a spaced-apart relationship in the form of wires or rods 106, 108. The rods 106, 108 are connected to switches 110, 112, respectively, located on the first portion 102. The switches 110, 112 are substantially similar to the switches 40, 42 of the embodiment of FIG. 1. However, as shown in FIG. 6, the switches 110, 112 are arranged such that both switches are normally open when the back of a user is in a state of proper posture. The switch 110 is arranged such that flexion of the back causes the rod 106 to pull the spring-biased contact arm 114 into the closed position, thereby activating an alarm signal. The switch 112 is arranged such that extension of the back causes the rod 108 to push the spring-biased contact arm 116 into the closed position, also activating an alarm signal. The device 100 further comprises warning signal mechanisms in the form of LEDs 132, 134, a speaker 136, and a vibrator motor 138. A three-position switch 140 controls the warning signal mode produced when either of the switches 110, 112 are activated (e.g., audible warning, visual warning, tactile warning, or any combination thereof). In this manner, the device 100 is configured to warn the user when the user is approaching an undesirable degree of flexion or extension.

Figure 6A:
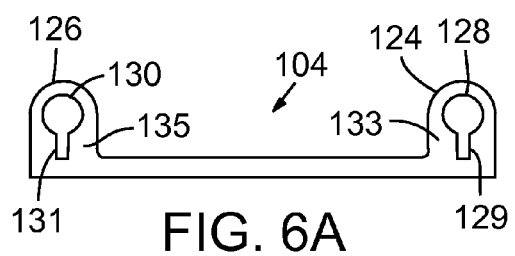
FIG. 6A is a side elevation view of the second mounting portion of the apparatus of FIG. 6.

Desirably, the wires or rods 106, 108 exhibit sufficient rigidity to transmit compressive force to the contact arms of the switches, yet are sufficiently elastic to allow the user to flex and extend their back. Suitable materials from which the rods 106, 108 can be formed include, without limitation, plastic, metal, wood, etc. In the embodiment shown, the rods 106, 108 comprise a plurality of enlargements or beads 118, 120 interspersed along the length of the rods 106, 108, respectively. The second mounting bracket 104 comprises a plate 122 having a pair of upstanding flanges 124, 126. The flanges 124, 126 comprise respective keyhole openings 128, 130 for receiving the beads, and narrow slots 129, 131 extending downward from the openings 128, 130 for receiving the portion of the rods extending between the beads, as shown in FIG. 6A. Desirably, the width of the slots 129, 131 is approximately equal to the diameter of the rods 106, 108. In this manner, the beads can be slipped through the openings 128, 130 to adjust the effective length of the rods. Once the desired effective length is reached, the rods can be pushed down into the slots 129, 131 such that the beads engage the walls 133, 135 of the flanges 124, 126 so as to trap the respective rod 106, 108 in an adjusted position. In this manner, the distance between the first mounting bracket 102 and the second mounting bracket 104 can be adjusted, thereby defining the degree of flexion or extension required to close the contact arms of the switches.

In alternative embodiments, the rods 106, 108 can comprise first portions 106a, 108a, and second portions 106b, 108b, as indicated in FIG. 6. The first portions 106a, 108a can include the beads 118, 120, respectively, and can be fabricated from suitably rigid materials such as plastic or metal. The beads 118, 120 can be integrally molded portions of the first portions, 106a, 108a. The second portions 106b, 108b can comprise elastic members such as elastic cords. The respective portions can be joined together by, for example, couplings or fasteners (not shown). In this manner, the rods 106, 108 can achieve a greater degree of flexibility, thereby allowing a wider range of motion in flexion and extension.

Figure 7A:
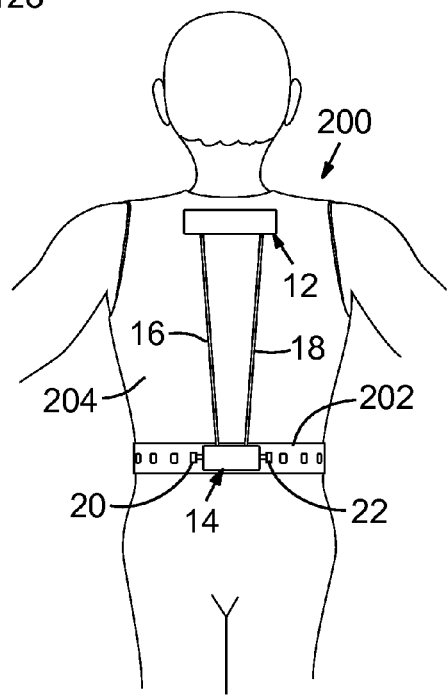
FIG. 7A is a side elevation view of an alternative embodiment of the apparatus of FIG. 1 being worn on a user's back.
Figure 7B:
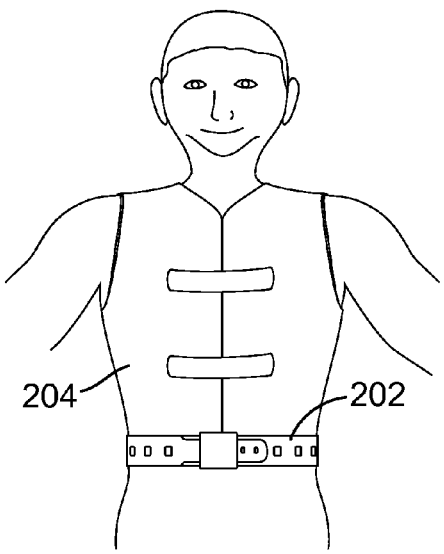
FIG. 7B is a front view of the user of FIG. 7A.

Referring now to FIGS. 7A-B, there is shown another embodiment of a device 200 configured to be worn on a user's back to treat or prevent poor posture. The device 200 is substantially similar to the embodiment of FIG. 1, with the exception that the first mounting portion or mounting bracket 12 is located on the upper back of the user in the thoracic region of the spine generally between the shoulders, while the second mounting portion or mounting bracket 14 is located on the lower back of the user generally over the lumbar region of the spine. The switches, alarms, and other electronic components (as shown in FIG. 1) can be mounted on the first mounting bracket 12. The second mounting bracket can be connected to a belt 202, which can be integrated with, or separate from, a vest 204 or another type of upper body garment or flexible back brace. Additionally, the rods 20, 22, which are coupled to the lower ends of the cords 16, 18, can be oriented horizontally. In this orientation the rods 20, 22 can adjust the length and tension of the cords 16, 18 by, for example, winding or unwinding the cords from spools (not shown) located on the second mounting bracket 14. Alternatively, the cords can wind or spool around the shafts of the rods 20, 22 as the rods are rotated, similar to tightening or loosening the strings of a guitar. In alternative embodiments, the device 200 can be mounted on the front or either side of the vest 204 and the belt 202.

Figures 8A, 8B:
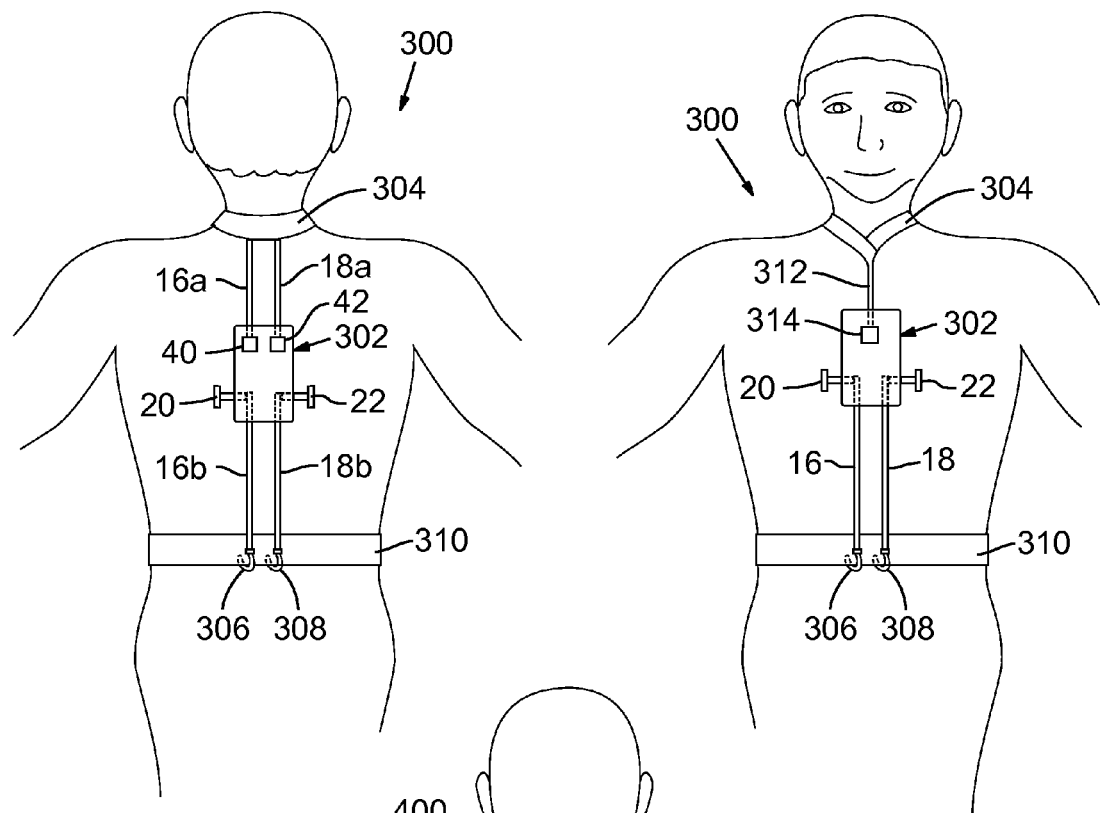
FIG. 8A is a side elevation view of another embodiment of an apparatus for warning a user about undesirable motion of a first portion of the user's body relative to a second portion of the user's body being worn by a user.
FIG. 8B is a side elevation view of an alternative embodiment of the apparatus of FIG. 8A being worn by a user.

Referring to FIGS. 8A-B, there is shown another embodiment of a device 300. The device 300 is substantially similar to the embodiments of FIGS. 1 and 7A-B, with the exception that the first and second mounting brackets 12, 14 are combined into a single mounting portion or mounting bracket 302. The mounting bracket 302 is configured to be worn over a user's clothing and, thus, does not require a vest. The mounting bracket 302 is suspended by cords 16a, 18a of fixed length that extend upward from the top portion of the mounting bracket 302 and are attached to a collar 304 worn around the user's neck. The cords 16b, 18b extend downward from the bottom portion of the mounting bracket 302, and comprise hooks 306, 308 configured to secure the cords to a conventional belt 310 worn by the user. The device 300 includes rods 20, 22 coupled to the cords 16b and 18b, and oriented horizontally on the mounting bracket 302. The rods 20, 22 are configured to adjust the length and tension of the cords 16b, 18b by, for example, winding the cords around spools (not shown) located on the body portion or winding the cords around the shafts of the rods. In this manner, the device 300 may be used to monitor the user's degree of flexion and extension while allowing the user to wear substantially any clothing that the user desires.

The switches, alarms, controller, and other electronic components (as shown in FIG. 1) can be mounted on the mounting bracket 302, and the cords 16a, 18a can be connected to the switches 40, 42, respectively. Alternatively, the cords 16b, 18b can be connected to the switches 40, 42, and the lengths of the cords 16a, 18a can be adjustable by rotating the rods 20, 22. In another alternative embodiment shown in FIG. 8B, cords 16, 18 can extend downwardly from the mounting bracket 302 and the device can be suspended from the collar 304 by a single cord 312 connected to a switch 314. The device 300 may also be worn on the chest or abdomen of a user, as shown in FIG. 8B. In yet another alternative embodiment, the cords 16b, 18b of FIG. 8A or the cords 16, 18 of FIG. 8B can be secured to a user's leg or legs, such as by securing the cords to a belt or wrap that is worn around the user's leg.

Figure 9:
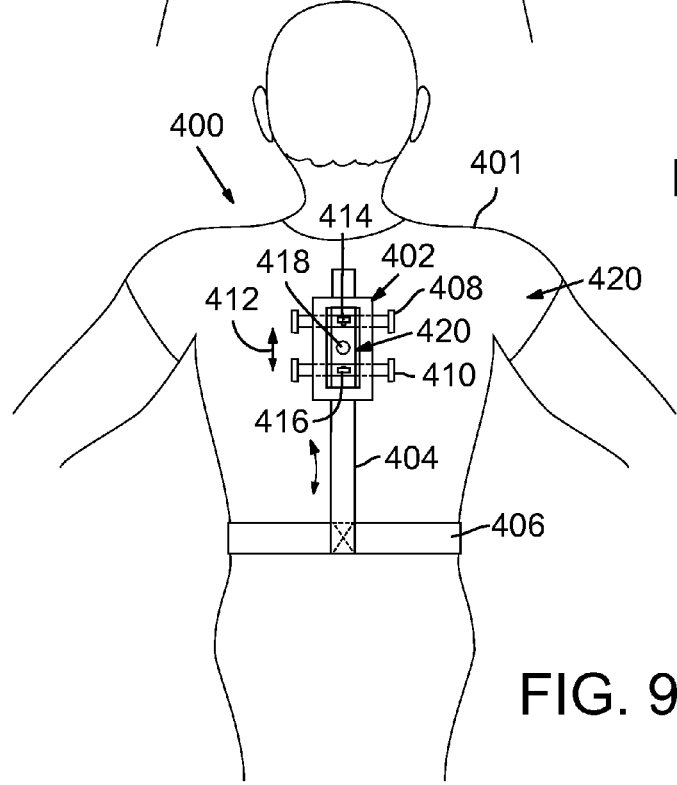
FIG. 9 is a side elevation view of another embodiment of an apparatus for warning a user about undesirable motion of a first portion of the user's body relative to a second portion of the user's body being worn by a user.
Figure 10A:
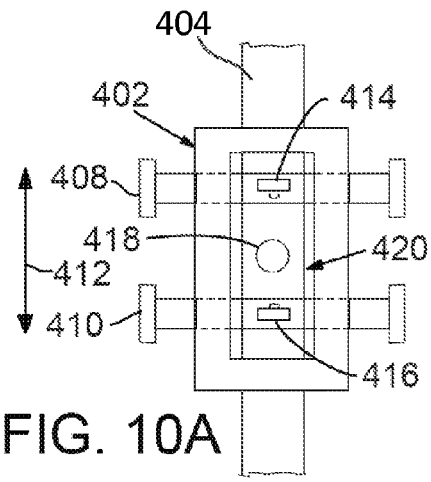
FIG. 10A is a magnified view of the switch assembly of the apparatus of FIG. 9.

Referring now to FIGS. 9 and 10A, there is shown another embodiment of a device 400 configured to be worn on a user's back to treat or prevent poor posture. The device 400 comprises a body, or housing 402, and an elongated flexible member 404 (e.g., a flexible rod or shaft) slidably disposed within the housing 402. As shown in FIG. 9, the device 400 can be mounted on a garment comprising a vest 401 and a belt 406. As shown, the housing 402 can be mounted on the back of the vest 401 and the flexible member 404 can be fixedly attached to the belt 406. Alternatively, the lower end of the flexible member 404 can be secured to a lower portion of the vest 401 or a shirt (not shown). Thus, as the user flexes or extends their back, the housing 402 moves relative to the flexible member 404 such that the flexible member is drawn through the housing 402 by the motion of the user. Rods 408, 410 are mounted to and extend through the housing 402 and may be translated or adjusted upward and downward relative to the housing in the directions indicated by arrow 412. The housing 402 defines a void or cutaway portion 420 (FIG. 10A), through which the rods 408, 410 and the flexible member 404 are exposed. As shown in FIG. 10A, switches, such as pushbutton switches 414, 416 can be mounted to the rods 408, 410 such that the switches 414, 416 protrude into the cutaway portion 420. In the embodiment shown, adjusting the distance between the rods adjusts the distance between the switches. In this manner, a user may set or adjust the range of motion by moving the switches closer together or farther away from one another by moving the rods.

The flexible member 404 can be, for example, a flattened or generally cylindrical rod or shaft, and can comprise a projection 418 which protrudes into the cutaway portion 420 of the housing such that it can contact the switches 414, 416 upon longitudinal movement of the flexible member 404. The flexible member 404 is configured such that as the user flexes their back, the projection 418 travels along the cutaway portion 420 until it contacts the switch 416, triggering an alarm signal and mechanically preventing further flexion. Similarly, as the user extends their back the projection 418 travels along the cutaway portion 420 in the opposite direction until it contacts the switch 414, thereby triggering an alarm signal and mechanically preventing further extension. The housing 402 can include a controller (not shown) similar to the controller 44 of FIG. 1, and warning signal mechanisms such as speakers, LEDs, vibrator motors, etc.

Figure 10B:
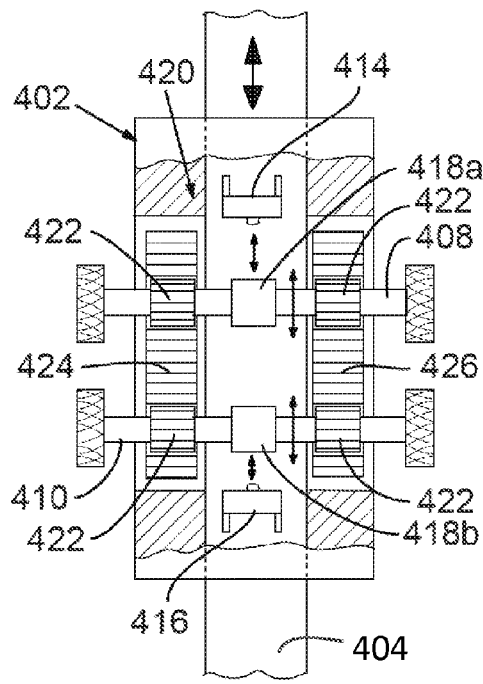
FIG. 10B is a magnified view of another embodiment of a switch assembly that can be used in the apparatus of FIG. 9.

Referring to FIG. 10B, there is shown an alternative embodiment of the device 400 of FIG. 9, wherein the rods 408, 410 comprise geared portions 422 disposed in tracks 424, 426 in the housing 402, such that rotating the rods 408, 410 causes them to translate linearly along the tracks, 424, 426. The rods 408, 410 can comprise projections 418a, 418b, respectively, that extend into the cutaway portion 420. Adjusting the distance between the rods adjusts the distance between the projections 418a, 418b. The switches 414, 416, are mounted to the flexible member 404 such that the distance between the switches 414, 416 is fixed. In this manner, adjusting the position of the rod 408 adjusts the distance between the projection 418a and the switch 414, and adjusting the position of the rod 410 adjusts the distance between the projection 418b and the switch 416. In this manner, the range of motion of the user's back can be established and adjusted.

In the embodiment shown, the projections 418a, 418b can comprise radial enlargements or protrusions that extend from the rods 408, 410 so as to contact the switches 416, 418 upon movement of the member 404. The housing 402 can include a controller similar to the controller 44 of FIG. 1 configured to execute the functionality of FIG. 11, and at least one warning signal mechanism such as a speaker, LED, vibrator motor, etc. As the user flexes their back, the switch 414 travels through the cutaway portion and can contact the projection 418a, triggering an alarm mechanism and mechanically preventing further flexion. Similarly, as the user extends their back, the switch 416 travels through the cutaway portion and can contact the projection 418b, triggering an alarm mechanism and mechanically preventing further extension. In alternative embodiments, the device 400 can comprise a single rod having a projection configured to contact either or both of the switches 414, 416. In other alternative embodiments, the switches can comprise other switch mechanisms such as limit switches, micro switches, optical switches, magnet switches, etc.

Figure 18:
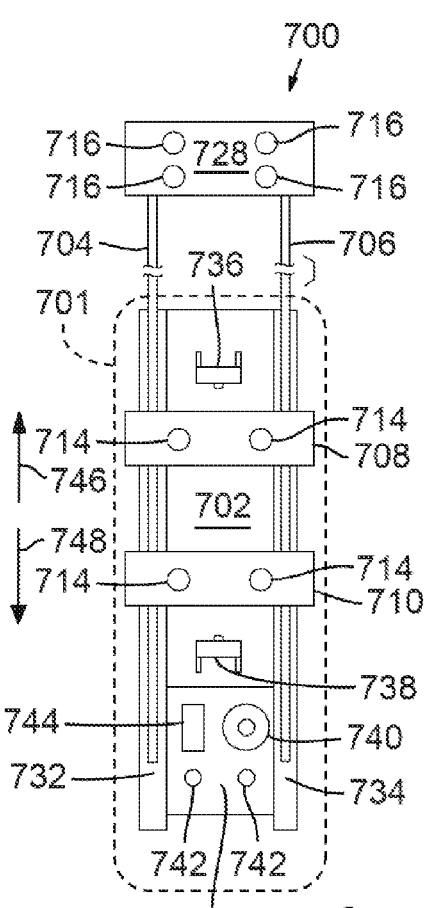
FIG. 18 is a plan view of another embodiment of an apparatus for warning a user about undesirable motion of a first portion of the user's body relative to a second portion of the user's body.

Referring to FIG. 18, there is shown another embodiment of a device 700, comprising a first mounting portion or mounting bracket 702 and a second mounting portion or mounting bracket 728. The first and second mounting brackets 702, 728 can be mounted to an upper body garment or back brace worn by a user such that the first mounting bracket 702 is disposed over the lumbar region of the spine and the second mounting bracket 728 is disposed over the thoracic region of the spine in a manner similar to the embodiment of FIG. 1. In alternative embodiments, the device 700 can be attached directly to the user's clothing, or directly onto the user's body, such as with an adhesive.

The first mounting bracket 702 can be mounted to a lower wall 701 of a housing that can extend around and contain the first mounting bracket 702. The first mounting bracket 702 can carry a controller 712 similar to the controller of FIG. 1, and warning signal mechanisms such as a speaker 740, LEDs 742, and a vibrator motor 744. The first mounting bracket 702 can also carry switches, such as pushbutton switches 736, 738, mounted in a fixed spatial relationship with one another.

The first mounting bracket 702 can be disposed between first and second elongated flexible members 704, 706. The first and second elongated members 704, 706 can be comprised of a flexible, semi-rigid material such as, for example, plastic or metal. The top portions of the elongated members 704, 706 can be fixedly attached to the second mounting bracket 728, which can comprise couplings or clamps (not shown) configured to receive the elongated members 704, 706. The clamps can be tightened or loosened with set screws 716. In this manner, the effective length of the elongated members 704, 706 can be adjusted. The bottom portions of the elongated members 704, 706 can be disposed in or coupled to the first mounting bracket 702, which can comprise grooves or tubes 732, 734 in which the elongated members 704, 706 can travel, respectively. In this manner, as the user flexes their back, the elongated members 704, 706 are pulled upward in the direction of arrow 746 and the elongated members can travel upward through the grooves or tubes 732, 734 relative to switches 736, 738. As the user extends their back, the elongated members are pushed downward in the direction of arrow 748 and the elongated members can travel downward through the grooves or tubes 732, 734 relative to switches 736, 738. The lower ends of the elongated members 704, 706 can remain in the grooves or tubes 732, 734 in both flexion and extension.

The elongated members 704, 706 are interconnected by two lateral cross members 708, 710 located between the switches 736, 738. The cross members 708, 710 can be adjustably attached to the first and second elongated members 704, 706 by clamps (not shown) having set screws 714, such that the cross members 708, 710 can be moved along the length of the first and second elongated members 704, 706 and clamped into position. The cross members 708, 710 are configured to travel with the elongated members 704, 706 as the elongated members 704, 706 are pulled upward in flexion or pushed downward in extension. As the elongated members 704, 706 travel upward in flexion, the cross member 708 can contact the switch 736, triggering an alarm signal and mechanically preventing further flexion. Similarly, as the elongated members 704, 706 travel downward in extension, the cross member 710 can contact the switch 738, triggering an alarm signal and mechanically preventing further extension. In this manner, adjusting the position of the cross members 708, 710 along the lengths of the first and second elongated members 704, 706 can define the user's range of motion in flexion and extension. In alternative embodiments, the device 700 can comprise one cross member configured to contact either or both of the switches 736, 738. In other alternative embodiments, the switches can comprise other switch mechanisms such as limit switches, micro switches, optical switches, magnet switches, etc.

Referring to FIGS. 13A-B, there is shown another embodiment of a device 500 configured to be worn by a user to treat or prevent poor posture. The device 500 comprises a first sensor 502, a second sensor 504, and a controller 510. The first sensor 502 is configured to be worn by the user on the upper torso, and is configured to measure the angle of flexion or extension of a user's torso relative to a predetermined reference angle or reference plane. The first sensor 502 can be worn on the chest, back, or sides of the torso on or underneath the arms. The second sensor 504 is configured to be worn at the level of the pelvis or waist (i.e., pelvic region), and is configured to measure the angle of flexion or extension of a user's waist relative to a predetermined reference angle or reference plane. In the embodiment shown, the first sensor 502 is configured to be worn on the side of the torso substantially beneath or behind the user's arm. In this manner, the degree of flexion or extension of the user's back can be monitored in any position (i.e., standing up, laying down, sitting, etc.) because the angle differential is measured as between the first and second sensors 502, 504, and not as compared to an absolute reference plane. The first sensor 502 and the controller 510 can be mounted on a flexible back brace 506 worn around the upper body of the user. The second sensor 504 can be mounted on a belt 508 worn around the waist of the user. The belt 508 can be an integral part of the brace 506 or a separate component.

Desirably, the reference plane can be a common reference plane for both sensors 502, 504, and can be a plane drawn through the spine in a neutral or proper posture, such as the frontal or coronal plane. As the user flexes or extends their back, the angle of deviation from the reference plane is measured by the first sensor 502 and compared to the angle of deviation from the reference plane measured by the second sensor 504. The user's permissible range of motion can be defined by a threshold angle differential as measured between the first sensor and the second sensor, beyond which further flexion or extension is undesirable, according to the particular circumstances of the user. As the user approaches or exceeds the threshold angle differential, the device 500 generates a warning signal (e.g., auditory, visual, tactile, etc.) to warn the user that they are approaching or have reached an unsafe degree of flexion (FIG. 13B) or extension. Sensors 502, 504 can comprise, for example, tilt sensors, accelerometers, inclinometers, clinometers, declinometers, slope gauges, pitch/roll indicators such as gradient meters, gradiometers, force-balance sensors, optical sensors, range sensors, distance sensors, proximity sensors, etc.

Figure 15:
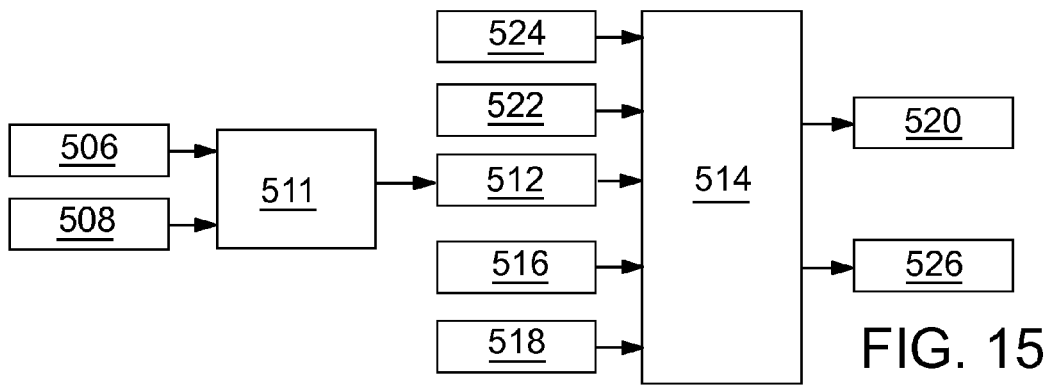
FIG. 15 is a schematic representation of a process performed by a controller of the apparatus of FIG. 13A.

The angle differential between the first sensor 502 and the second sensor 504 is monitored by the controller 510, which can be configured to execute the functionality shown in FIG. 15. In a first step, the angle readout 506 of the first sensor 502 and the angle readout 508 of the second sensor 504 are inputted into a first subroutine 510. The first subroutine 510 determines the difference between the angle readout 506 and the angle readout 508, wherein the difference between the readouts 506, 508 is the angle of flexion or extension 512 of the user's spine. The angle of flexion or extension 512 is then inputted into a second subroutine 514. The second subroutine 514 compares the angle of flexion or extension 512 to a predetermined threshold angle 516 determined by the user or the user's physician and inputted into the second subroutine 514. The time duration for which the angle of flexion or extension 512 is maintained by the user is monitored and compared to a predetermined time duration threshold 518, also determined by the user or the user's physician and inputted into the second subroutine 514. If the angle of flexion or extension 512 exceeds the predetermined angle 516 for the amount of time required by the time duration threshold 518 (e.g., 0 seconds, 1 second, 2 seconds, etc.), the second subroutine 514 generates an alarm signal output 520 in the form of a visual signal (e.g., LEDs, light bulbs, etc.), an auditory signal (e.g., speakers, buzzers, etc.), a tactile signal (e.g., vibrator motors, etc.), or any combination thereof. In the embodiment shown, the type of alarm signal generated can be determined by the user through an alarm mode input 522. The second subroutine 514 also comprises an ON/OFF input functionality 524, and is configured to perform a data output function 526 wherein data such as time, date, and the angle of flexion or extension can be outputted to non-transitory, computer-readable storage media or a computer for analysis. In alternative embodiments, the controller 510 can include a calibration function.

In alternative embodiments, the device 500 need only comprise one sensor. For example, the device 500 can comprise only the sensor 502 configured to be worn on the user's torso. The sensor 502 can be configured to measure the angle of flexion or extension of the user's torso relative to a reference plane, such as the coronal plane. In this manner, the angle of the user's torso can be measured only with respect to the reference plane of the sensor 502.

In an alternative embodiment, the device 500 can comprise a sensor 528 configured to bend or flex as the user flexes or extends their back, as shown in FIG. 14. The sensor 528 can be configured such that its electrical resistance changes as it flexes or extends along with flexion or extension of the user's back, such as a flexible potentiometer. In the embodiment shown, the sensor 528 is attached to a brace 506, although the sensor 528 can be worn on a vest or shirt similar to the device of FIG. 1, or can be attached directly to the user's body. Additionally, the sensor is depicted extending from substantially the thoracic region of the spine to the lumbar region of the spine. However, the sensor 528 can comprise any suitable length, and can be located at any suitable location on the user's torso. The embodiment of FIG. 14 also can comprise a controller mounted on the brace 506 configured to execute functionality similar to the functionality shown in FIG. 15.

Figures 16A, 16B:
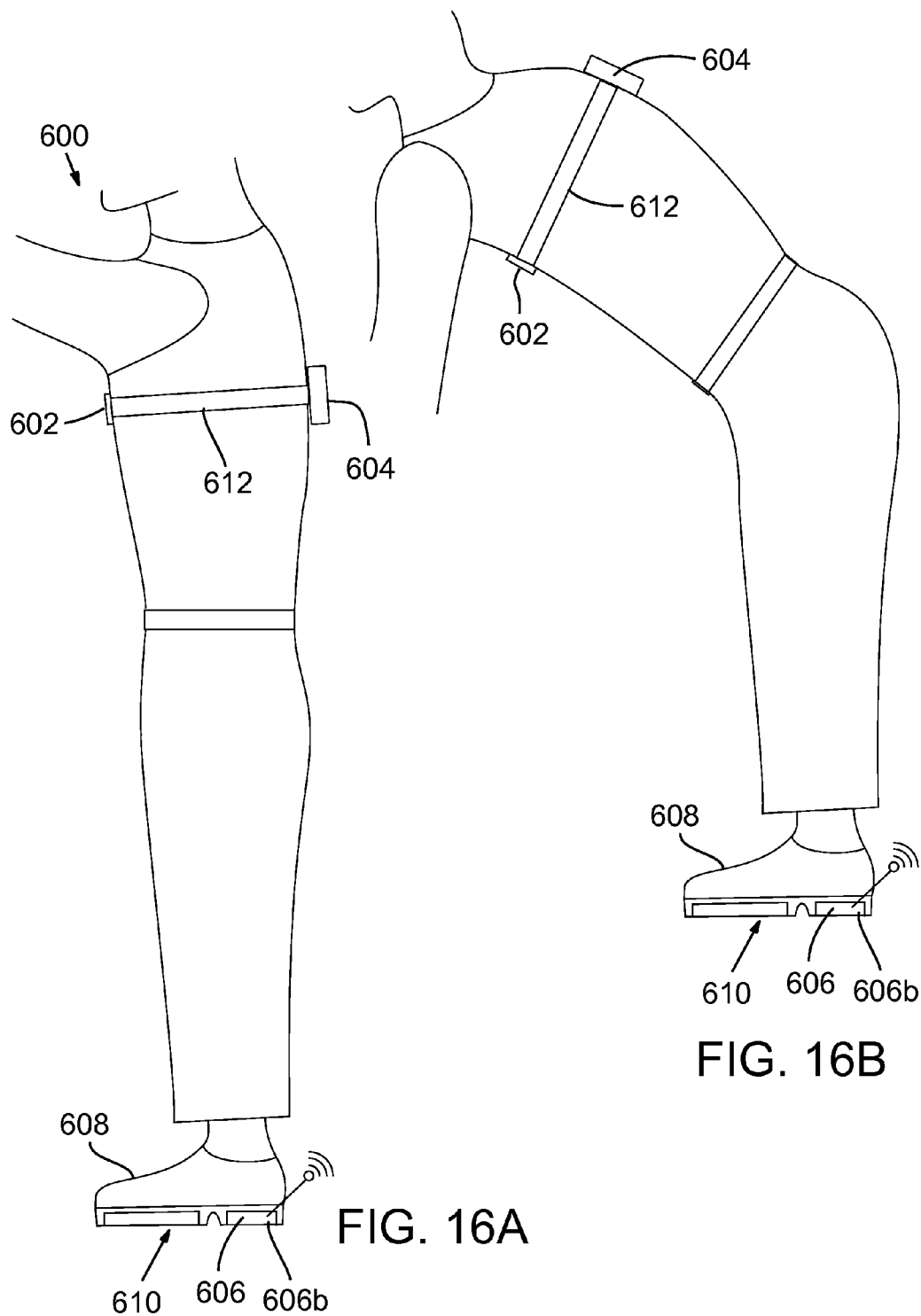
FIG. 16A is a side elevation view of a user wearing an apparatus for monitoring flexion and extension of the back and the weight of an objection being lifted by the user.
FIG. 16B is a side elevation view of a user bending forward wearing the apparatus of FIG. 16A.

Referring now to FIGS. 16A-B, there is shown another embodiment of a device 600 configured to be worn by a user to treat or prevent poor posture, particularly when lifting an object. More particularly, the device 600 is configured to warn (i.e., by generating a visual, audible, or tactile warning signal) a user when the user lifts or attempts to lift an object of undesirable weight at an undesirable angle of flexion or extension. The device 600 comprises at least one flexion/extension sensor 602 configured to be worn on the user's torso, a controller 604, and at least one force or load sensor 606. The sensor 602 is configured to measure the angle of flexion or extension of a user's back relative to a reference plane in a manner similar to the embodiment of FIGS. 13A-B, and is configured to electronically transmit the angle of flexion or extension to the controller 604. Desirably, the reference plane is the frontal or coronal plane. In the embodiment shown, the sensor 602 is located on the user's chest. However, the sensor 602 can be located at any suitable location on the user's torso, such as on the user's back, sides, etc. As shown, the sensor 602 and the controller 604 can be supported on a strap 612 that can be worn around the upper torso. In alternative embodiments, the sensor 602 and the controller 604 can be mounted on any suitable wearable device that can be worn on the torso, such as a brace, vest, shirt, etc. In further alternative embodiments, the sensor 602 can comprise two or more sensors arrayed on the torso or the waist in the manner of the embodiment of FIGS. 13A-B.

The load sensor 606 can be located beneath the user's feet such as in or on the user's shoe 608. In the embodiment shown, the load sensor 606 is located in the sole 610 of the shoe 608 immediately beneath the user's heel. The load sensor 606 is configured to sense the force bearing down on the user's shoe 608 and transmit the measured force value to the controller 604. In this manner, the load sensor 606 can measure the weight of an object (not shown) being held or lifted by the user. The load sensor 606 can be incorporated into the shoe during construction (i.e., built into the shoe), or can be configured as an attachment. The load sensor 606 can be configured to wirelessly transmit force value data to the controller 604, as shown in FIGS. 16A-B, or can transmit data via a wired connection. Desirably, each of the user's shoes comprises a load sensor 606, such that a first load sensor 606*a* is located on, for example, a user's right shoe, and a second load sensor 606*b* is located on, for example, a user's left shoe. However, alternatively, the device 600 can comprise a single load sensor.

Figure 17:
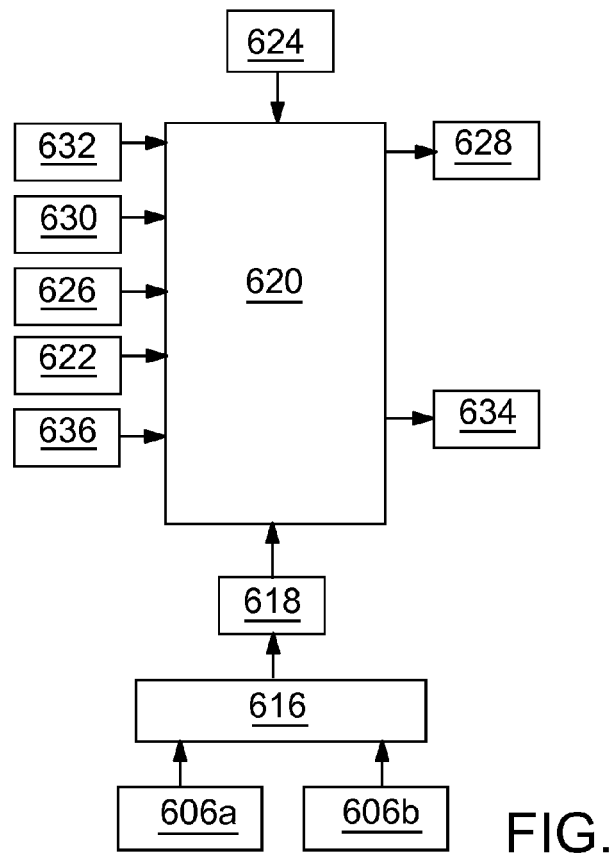
FIG. 17 is a schematic representation of a process performed by a controller of the apparatus of FIG. 16A.

The controller 604 is configured to execute the functionality shown schematically in FIG. 17. In a first step, the weight or force value measured by the first load sensor 606*a* and the force value measured by the second load sensor 606*b* are inputted into a first subroutine 616. The first subroutine 616 determines the total load 618 being supported by the user and hence the weight of any objects being carried or lifted by the user. The total load 618 is inputted into a second subroutine 620 where it is correlated with an angle of flexion or extension 622 as measured by the sensor 602, and a time duration input 626 corresponding to the time duration of the user's flexion or extension.

Figure 19:
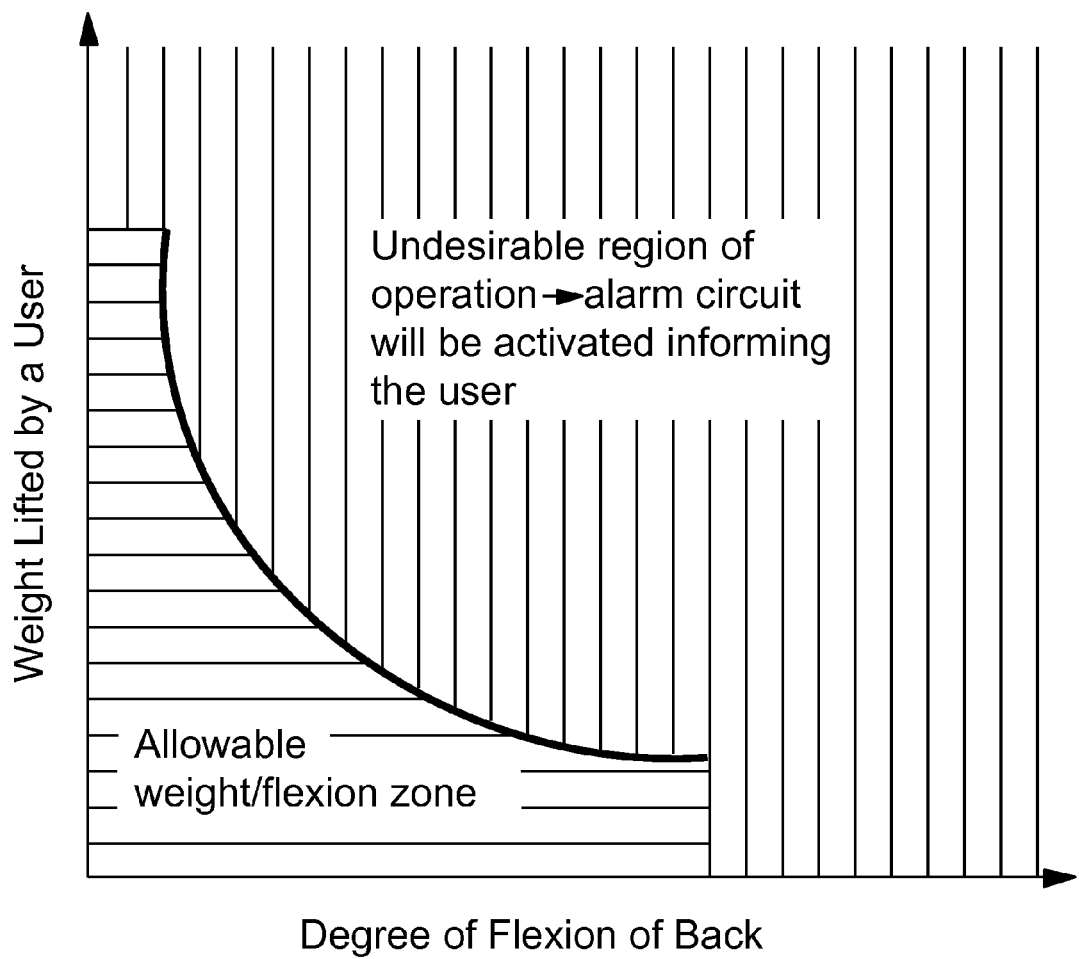
FIG. 19 is a chart showing a representative relationship between an allowable weight lifted by a user and a degree of flexion of the user's back.

The second subroutine 620 compares the angle of flexion or extension 622, the total load 618, and the time duration 626 to a pre-programmed table or matrix 624 containing allowable loads (i.e., allowable weight limits or predetermined weights) and time durations for given angles of flexion and extension as determined by the user or the user's physician. If any of the total load 618 or time duration 626 parameters exceed the allowable values for the measured angle of flexion or extension 622 as determined by the matrix 624, the second subroutine 620 generates an alarm signal output 628. Similar to the embodiment of FIG. 15, the alarm signal output 628 can be in the form of a visual signal (e.g., LEDs, incandescent lights, etc.), an auditory signal (e.g., speakers, buzzers, etc.), a tactile signal (e.g., vibrator motors, etc.), or any combination thereof, as determined by the alarm mode selector input 630. The chart of FIG. 19 shows a graphical representation of a matrix 624 depicting a representative relationship between the weight of an object lifted by the user and an allowable degree of flexion. The second subroutine 620 also comprises an ON/OFF input functionality 632, and is configured to perform a data output function 634 wherein data such as time, date, angle of flexion or extension, total load, and time duration of flexion or extension can be outputted to non-transitory, computer-readable storage media or a computer for analysis. In the embodiment shown, the second subroutine also comprises a calibration input 636, wherein the user's weight can be inputted before use of the device 600. In alternative embodiments, the load sensors and controller of FIGS. 16A-B can be used with any of the embodiments of FIGS. 1-15 and 17-18.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. I therefore claim as my invention all that comes within the scope and spirit of these claims.

I claim:

1. An apparatus for warning a user about motion of a first portion of the user's body relative to a second portion of the user's body, comprising:
    a first sensor mountable on the first portion of the user's body and configured to measure an angle of the first portion of the user's body relative to a reference;
    a second sensor mountable on the second portion of the user's body and configured to measure an angle of the second portion of the user's body relative to the reference;
    a controller in communication with the first and second sensors;
    a warning mechanism in communication with the controller;
    wherein the controller determines a difference between the angle of the first portion of the user's body and the angle of the second portion of the user's body indicative of an amount of movement of the first portion of the user's body relative to the second portion of the user's body, and activates the warning mechanism when the difference is beyond a predetermined angle.

2. The apparatus of claim 1, wherein the predetermined angle is an angle of flexion.

3. The apparatus of claim 1, wherein the predetermined angle is an angle of extension.

4. The apparatus of claim 1, wherein the first portion of the user's body is an upper portion of the torso and the second portion of the user's body is the pelvic region.

5. The apparatus of claim 4, further comprising a load sensor configured to be placed on the bottom of a shoe of the user, the load sensor being configured to detect the weight of a load lifted by the user, wherein the controller is in communication with the load sensor and is operable to activate the warning mechanism if the weight of the load exceeds a predetermined weight.

6. The apparatus of claim 5, wherein the controller is operable to determine a weight limit corresponding to an angle of flexion of the torso and activate the warning mechanism if the weight of the load lifted by the user exceeds the weight limit.

7. The apparatus of claim 1, wherein the warning mechanism comprises at least one of a speaker, a light-emitting diode, or a vibrator motor.

8. The apparatus of claim 1, wherein at least one of the first or second sensors comprises an inclinometer.

9. The apparatus of claim 1, wherein the controller further comprises non-transitory computer-readable storage media for storing data relating to the motion of the first and second portions of the user's body.

10. An apparatus for warning a user about motion of a first portion of the user's body relative to a second portion of the user's body, comprising:
  a first sensor mountable on the first portion of the user's body and configured to measure an angle of the first portion of the user's body relative to a reference;
  a second sensor mountable on the second portion of the user's body and configured to measure an angle of the second portion of the user's body relative to the reference;
  a controller in communication with the first and second sensors;
  a warning mechanism in communication with the controller;
  wherein the controller determines a difference between the angle of the first portion of the user's body and the angle of the second portion of the user's body indicative of an amount of movement of the first portion of the user's body relative to the second portion of the user's body, and activates the warning mechanism when the difference is beyond a predetermined angle;
  wherein the predetermined angle is a first predetermined angle; and
  wherein the controller is configured to compare the angle of the first portion of the user's body with the first predetermined angle and the angle of the second portion of the user's body with a second predetermined angle.

11. An apparatus for maintaining a neutral orientation of a user's spine, comprising:
  a mounting portion configured to be placed on the user's upper body;
  at least one elongated member extending from the mounting portion to a pelvic region of the user;
  a switch mechanism coupled to the mounting portion;
  a switch activation member coupled to the elongated member and movable longitudinally therewith and operable to activate the switch mechanism; and
  a warning mechanism electrically coupled to the switch mechanism;
  wherein at least one of the mounting portion or the elongated member is movable relative to the other upon flexion or extension of the user's spine, and the warning mechanism is operable to warn the user of flexion or extension of the spine beyond a predetermined range of motion upon activation of the switch mechanism by the switch activation member.

12. The apparatus of claim 11, further comprising a wearable device configured to be worn on the user's upper body, the mounting portion being mounted on a lower portion of the wearable device.

13. The apparatus of claim 12, wherein the wearable device comprises a back brace.

14. The apparatus of claim 12, wherein the wearable device comprises a shirt or a vest.

15. The apparatus of claim 11, further comprising a motion limiting member configured to limit movement of the elongated member so as to prevent extension or flexion of the spine beyond the predetermined range of motion.

16. The apparatus of claim 11, wherein the switch mechanism is a magnet switch.

17. The apparatus of claim 11, wherein the mounting portion is suspended from a collar portion configured to be worn around a user's neck.

18. The apparatus of claim 11, further comprising a controller electrically coupled to the switch mechanism and the warning mechanism, and operable to activate the warning mechanism upon activation of the switch mechanism by the switch activation portion.

19. The apparatus of claim 18, further comprising a load sensor configured to be placed on the bottom of a shoe of the user, the load sensor being configured to detect the weight of a load lifted by the user; and
  wherein the controller is in communication with the load sensor and is operable to activate the warning mechanism if the weight of the load exceeds a predetermined weight.

20. The apparatus of claim 19, wherein the controller is operable to determine a weight limit corresponding to an angle of flexion of the upper body and activate the warning mechanism if the weight of the load lifted by the user exceeds the weight limit.

21. The apparatus of claim 11, wherein the elongated member comprises an elastic material.

22. A method of using the apparatus of claim 11, comprising:
  placing the mounting portion on the upper body such that the elongated member extends from the mounting portion to the pelvic region; and
  flexing or extending the spine such that the switch activation member activates the switch mechanism when flexion or extension of the spine is beyond the predetermined range of motion.

* * * * *